United States Patent [19]

Collins et al.

[11] 4,064,350
[45] Dec. 20, 1977

[54] 15,16-DIHYDROXYPROSTAGLANDINS

[75] Inventors: Paul W. Collins, Deerfield; Raphael Pappo, Skokie, both of Ill.

[73] Assignee: G. D. Searle & Co., Chicago, Ill.

[21] Appl. No.: 744,070

[22] Filed: Nov. 22, 1976

[51] Int. Cl.² .................................................. C07C 177/00
[52] U.S. Cl. .............................. 560/121; 260/345.9 P; 260/438.1; 260/448.8 R; 260/514 D; 424/305; 424/317
[58] Field of Search ..................... 260/468 D, 514 D

[56] References Cited
FOREIGN PATENT DOCUMENTS 7,608,248  1/1976  Japan .................................... 260/468

Primary Examiner—Robert Gerstl
Attorney, Agent, or Firm—John J. McDonnell

[57] ABSTRACT

The present invention encompasses compounds of the formula:

wherein one of A and B is methyl and the other is hydrogen, the wavy line represents R or S stereochemistry, $n$ is 2–5, and R is hydrogen or lower alkyl having 1–7 carbon atoms.

4 Claims, No Drawings

15,16-DIHYDROXYPROSTAGLANDINS

The present invention encompasses compounds of the formula:

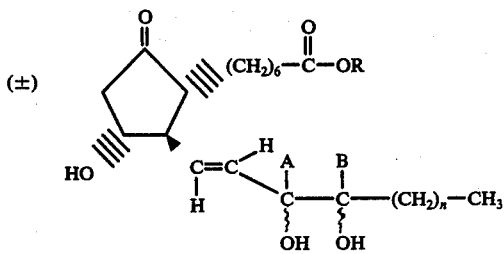

wherein one of A and B is methyl and the other is hydrogen, the wavy line represents R or S stereochemistry, n is 2–5, and R is hydrogen or lower alkyl having 1–7 carbon atoms.

Preferred compounds are of the formula

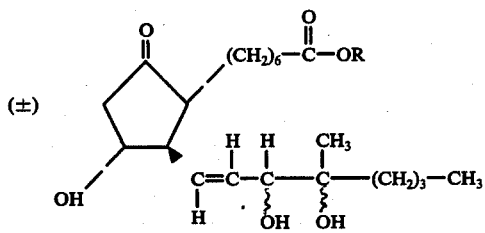

wherein R represents hydrogen or lower alkyl having 1–7 carbon atoms and the wavy line represents R or S stereochemistry.

±Refers to the compound shown and its mirror immage with regard to the stereochemistry about the 1, 2, and 3 positions of the 5 membered ring i.e. α,β, α and β,α,β.

Specific compounds in the scope of the present invention are:

methyl 7-[(3α-hydroxy-2β-(4(R)-hydroxy-4-methyl-3(S)hydroxy trans-1-octen-1-yl)-5-oxocyclopent-1α-yl]heptanoate.

methyl 7-[(3α-hydroxy-2β-(4(S)-hydroxy-4-methyl-3(S)hydroxy trans-1-octen-1-yl)-5-oxocyclopent-1α-yl]heptanoate.

methyl 7-[(3α-hydroxy-2β-(4(R)-hydroxy-4-methyl-3(R)hydroxy trans-1-octen-1-yl)-5-oxocyclopent-1α-yl]heptanoate.

methyl 7-[(3α-hydroxy-2β-(4(S)-hydroxy-4-methyl-3(R)hydroxy trans-1-octen-1-yl)-5-oxocyclopent-1α-yl]heptanoate.

methyl 7-[(3β-hydroxy-2α-(4(R)-hydroxy-4-methyl-3(S)hydroxy trans-1-octen-1-yl)-5-oxocyclopent-1β-yl]heptanoate.

methyl 7-[(3β-hydroxy-2α(4(S)-hydroxy-4-methyl-3(S)hydroxy trans-1-octen-1-yl)-5-oxocyclopent-1β-yl]heptanoate.

methyl 7-[(3β-hydroxy-2α-(4(R)-hydroxy-4-methyl-3(R)hydroxytrans-1-octen-1-yl)-5-oxocyclopent-1β-yl]heptanoate, methyl 7-[(3β-hydroxy-2α-(4(S)-hydroxy-4-methyl-3(R)hydroxytrans-1-octen-1-yl)-5-oxocyclopent-1β-yl]heptanoate.

Compounds of the present invention are prepared by the methods set out in Scheme I as follows:

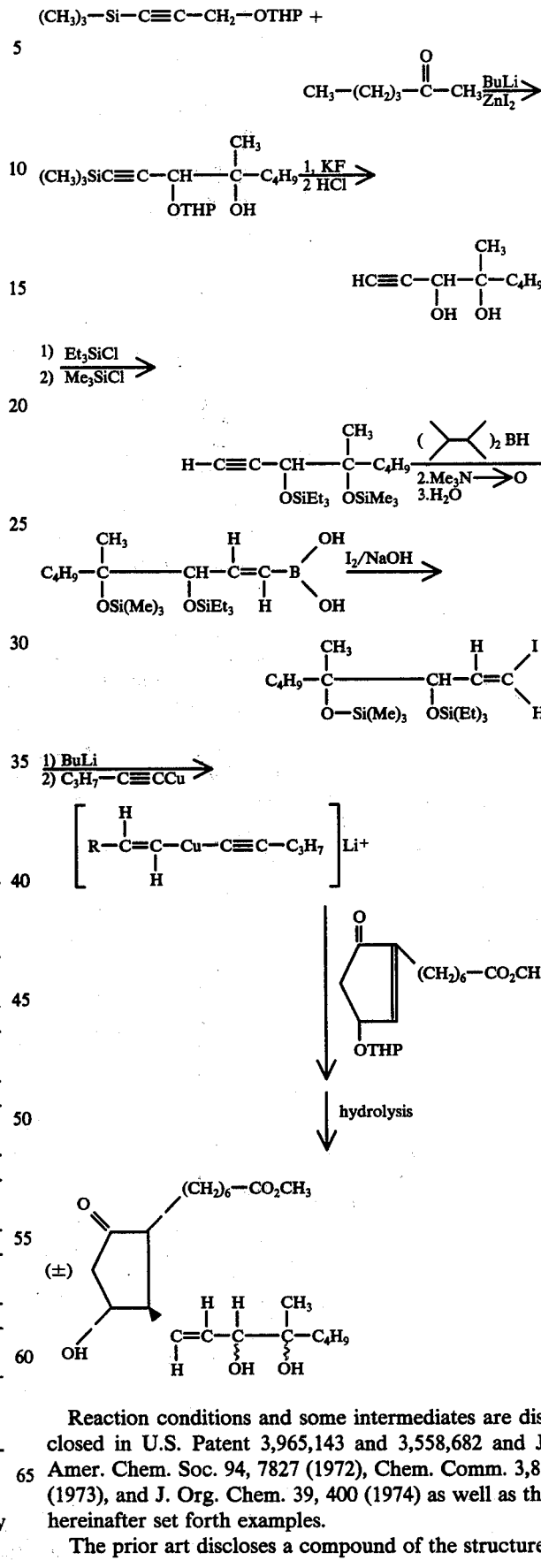

Reaction conditions and some intermediates are disclosed in U.S. Patent 3,965,143 and 3,558,682 and J. Amer. Chem. Soc. 94, 7827 (1972), Chem. Comm. 3,88 (1973), and J. Org. Chem. 39, 400 (1974) as well as the hereinafter set forth examples.

The prior art discloses a compound of the structure

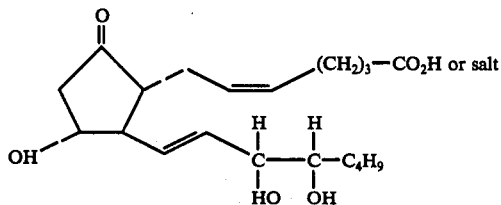

disclosed in Japanese Patent Application JA 078464 on July 9, 1974. Compounds of the present invention are particularly distinct in that they have a methyl group at C-16 and they are saturated at $C_5$-$C_6$.

Compounds of the structure

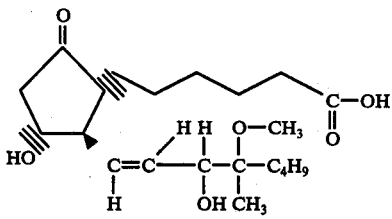

are disclosed in German Offenlegungsschrift No. 2601646, July 29, 1976. Compounds of the present invention are structurally distinct in that they are 16-hydroxy rather than 16-ether compounds.

The novel compounds of the present invention display valuable pharmacolocical properties as is exemplified by their ability to inhibit the gastric secretion stimulated by secretogogues such as histamine and pentagastrin.

The specific assay used to detect gastric antisecretory activity is described as follows:

Adult female beagle dogs weighing 13-20 kg are prepared with denervated fundic Heidenhain pouches. After a recovery period of at least 4 weeks following surgery, the animls are fasted for approximately 20 hours, then are placed in Pavlov stands and infused intravenously with saline solution. The pounched secretions are collected every 15 minutes and measured for volume and total acidity by tritration with 0.1 N sodium hydroxide to pH 7.0. Following a 30 minute basal secretion the dogs are infused with a saline solution of histamine dihydrochloride at a dose of 1.0 mg/hr. The volume of the diffusion is kept at approximately 13 ml/hr. A steady state plateau of gastric secretion is obtained approximately 1 hour following the start of histamine infusion at the end of which time the test compound dissolved in an ethanolic iso-osmotic phosphate buffer solution is administered by a single intravenous injection. The duration of the anti-secretory effects is determined and the side-effects, if any, recorded. The compound is rated active if statistically significant inhibition of secretory parameters occur following compound treatment.

The compounds of the present invention are combined with common pharmaceutical carriers and administered to animals in need of antisecretory treatment. For example, propantheline bromide described in Cuttings Handbook of Pharmacology, 4th edition, Appleton-Century Crofts, N.Y., N.Y., page 548, is active in the above test.

The invention will appear more fully from the examples which follow. The examples are given by way of illustration only and are not to be construed as limiting the invention either in spirit or in scope as many modifications both in materials and methods will be apparent to those skilled in the art. In these examples temperatures are given in degrees centigrade (° C.) and quantities of materials in parts by weight unless otherwise noted.

EXAMPLE 1

To 24.4 parts of 3-tetrahydropyranyloxy-1-propyne dissolved in 300 parts by volume of anhydrous ether and cooled to −50° C is added 74 parts by volume of 2.4 molar n-butyl lithium in hexane. The mixture is stirred for 45 minutes and allowed to warm to 30° C and then 19.3 parts of trimethylsilyl chloride in 50 parts by volume of dry ether is added and the mixture allowed to stand for about 12 hours. The mixture is cooled to 5° C and water is added. The ethereal layer is washed with water, saturated sodium chloride, and dried over anhydrous sodium sulfate. The solvent is removed and the residual liquid is distilled at 0.20 mm at 67°-69° to provide 1-trimethylsilyl-3-tetrahydropyranyloxy-1-propyne (Tetrahedron 29, 883 (1973)).

To 13.6 parts of the above ether in 100 parts by volume of tetrahydrofuran at −70° C is added 37 parts by volume of 2.4 molar butyl lithium in hexane. This mixture is stirred for 20 minutes at −70° C and the solution is allowed to stand for 45 minutes and then 17.8 parts of zinc iodide in 350 parts by volume of tetrahydrofuran is added while maintaining the temperature at −70° C. The resulting yellow solution is stirred for 1 hour and 8 parts of 2-hexanone in 50 parts by volume of tetrahydrofuran is added while retaining the temperature at −70° C. The reaction mixture is allowed to warm to −30° C, water is carefully added, and the reaction mixture is allowed to come to room temperature. The reaction mixture is extracted with ether, washed with water and saturated sodium chloride, and dried over anhydrous sodium sulfate. The solvent is stripped and the residual oil is distilled at 107°-110° C/0.5 mm to provide 1-trimethylsilyl-3-tetrahydropyranyloxy-4-methyl-1-octyne.

7 Parts of this ether and 7 parts of potassium fluoride are placed in 7.5 parts by volume of dimethylformamide and stirred at room temperature for 3 hours. The reaction mixture is poured into water and extracted with ether. The ether extracts are washed with water and dried over anhydrous sodium sulfate. Removal of solvent provides 4-hydroxy-4-methyl-3-tetrahydropyranyloxy-1-octyne and this material is hydrolysed in 50 parts by volume of acetic acid, 20 parts by volume of tetrahydrofuran, and 20 parts by volume of water by stirring the mixture for 10 hours at room temperature and then heating the mixture at 60°-70° C for two hours. The reaction mixture is poured into a mixture of ethyl acetate/ether/water and the organic layer is separated. The organic layer is washed with water and dilute sodium hydroxide. The organic layer is dried over anhydrous sodium sulfate and the solvent removed. Chromatography on silica gel with elution in 40% ethyl acetate/hexane provides 3,4-dihydroxy-4-methyl-1-octyne.

2.5 Parts of this diol, 3 parts of triethylsilyl chloride, and 4 parts of imidazole are reacted in 10 parts by volume of dimethylformamide. Thin layer chromatograhy indicated only one hydroxyl group to be silylated and then 1.65 parts of trimethylsilyl chloride are added to the reaction mixture to provide 3-triethylsilyloxy-4- trimethylsilyloxy-4-methyl-1-octyne which is purified by low pressure chromatography on silica gel with elution in 5% ethyl acetate/hexane.

1.1 Parts by volume of 1 molar BH₃ in tetrahydrofuran is cooled to 0° C and 0.154 parts of 2-methyl-2-butene is added to provide a solution of disiamylborane and to this solution is added 0.342 parts of 3-triethylsiloxy-4-trimethylsilyloxy-4-methyl-1-octyne. The reaction mixture is stirred for 10 hours at room temperature and then 0.5 parts of trimethylamine N-oxide is added and the mixture is stirred for 2 hours. This reaction mixture is taken up in ether and the ether solution is washed with dilute hydrochloric acid, water, and dried over sodium sulfate. Removal of the solvent and purification by low pressure chromatography on silica gel using 20% ethyl acetate/hexane as eluent provides 3-triethylsilyloxy-4-methyl-4-trimethylsilyloxy-trans-1-octenyl boronic acid. 1.94 Parts of this alkenyl boronic acid is dissolved in 10 parts by volume of methanol, cooled to 0° C and treated with 0.8 part sodium hydroxide in parts by volume of water. To this solution is added dropwise at 0° C a solution of 2.5 parts of iodine in 30 parts by volume of methanol. The reaction mixture is poured into a mixture of 200 parts ether/100 parts water. The organic layer is separated and washed with water containing 1% sodium sulfite, and then with pure water. The organic layer is dried with sodium sulfate and the solvent removed. Low pressure chromatography on silica gel using hexane as the eluent provides 3(RS),4(RS)-3-triethylsilyloxy-4-trimethylsilyloxy-4-methyl trans-1-octenyl iodide having the structural formula:

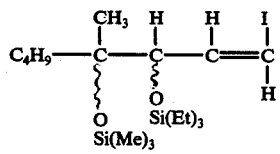

0.940 Part of this vinyl iodide is dissolved in 5 parts by volume of ether and cooled to −60° C and to this solution is added 0.8 part by volume of 2.5 molar butyl lithium.

In a separate reaction vessel 0.26 part of copper 1-pentyne is suspended in 3 parts by volume of ether and treated with 0.65 part of hexamethylphosphorus triamide. This mixture is stirred until a homogeneous solution is obtained. This homogeneous solution is added to the previous reagent solution and then 0.6 part of racemic methyl 7-(3-tetrahydropyran-2-yloxy-5-oxocyclopent-1-ene)heptanoate in 10 parts by volume of ether. The reaction mixture is stirred at −60° C for 1 hour, then poured into a mixture of ether and dilute HCl solution. The ether layer is washed with water three times, filtered, dried with sodium sulfate and chromatographed on silica gel using 30% ethyl acetate/hexane as eluent to provide a compound of the formula:

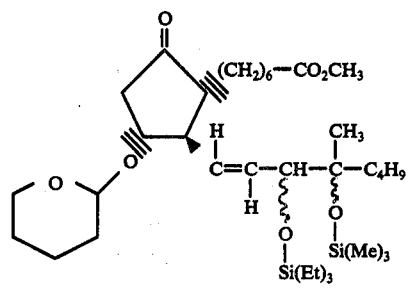

and the mirror image thereof.

The protecting groups are removed from the hydroxyl groups by 10 hour hydrolysis in a 3:1:1 mixture of acetic acid-tetrahydrofuran:water at room temperature. Chromatography on silica gel eluting with ethyl acetate provides methyl 7-[(3α-hydroxy-2β-(4(RS)-4-hydroxy-4-methyl-3(S)-hydroxy-trans-1-octen-1-yl)-5-oxocyclopent-1α-yl]heptanoate and the mirror image thereof and having the following structural formula:

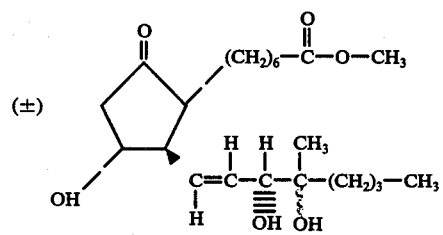

and methyl 7-[(3α-hydroxy-2β-(4(RS)-4-hydroxy-4-methyl-3(R)-hydroxy-trans-1-octen-1-yl)-5-oxocyclopent-1α-yl]heptanoate and the mirror image thereof and having the following structural formula:

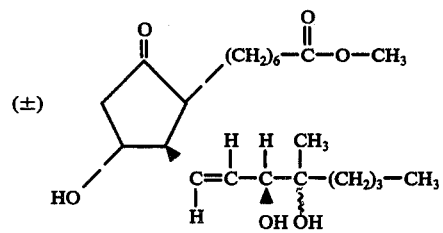

as separate compounds.

EXAMPLE 2

The substitution of an equivalent quantity of tetrahydropyran-2-yl 7-(3(RS)-tetrahydropyran-2-yloxy-5-oxocyclopent-1-ene)heptanoate in the procedure of Example 1 affords racemic 7-[(3α-hydroxy-2β-(4-(RS)-4-hydroxy-4-methyl-3(S)-hydroxy-trans-1-octen-1-yl)-5-oxocyclopent-1α-yl]heptanoic acid and racemic 7-[(3α-hydroxy-2β-(4(RS)-4-hydroxy-4-methyl-3(R)-hydroxy-trans-1-octen-1yl)-5-oxocyclopent-1α-yl]heptanoic acid.

EXAMPLE 3

Following the procedure in Example 1 and replacing 2-hexanone with 2-octanone provides ± methyl 7-[(3α-hydroxy-2β-4(RS)-hydroxy-4-methyl-3(RS)-hydroxy-trans-1-decen-1-yl)-5-oxocyclopent-1α-yl]heptanoate having the following structural formula:

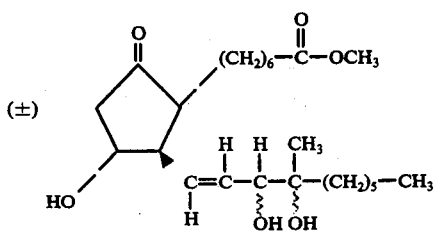

EXAMPLE 4

Following the procedure set out in Example 1 replacing 3-tetrahydropyranyloxy-1-propyne with equivalent quantities of 3-tetrahydropyranyloxy-1-butyne and replacing 2-hexanone with an equivalent quantity of pentanal provides ± methyl 7-[(3α-hydroxy-2β-(4(RS)-hydroxy-3-(RS)-hydroxy-3-methyl trans-1-octen-1-yl)-5-oxocyclopent-1α-yl]heptanoate, having the formula:

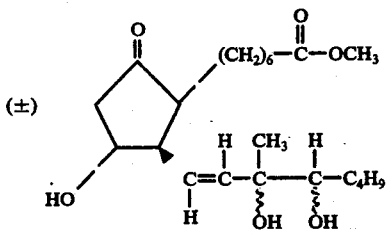

What is claimed is:

1. A compound of the formula

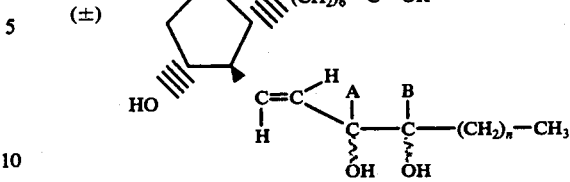

wherein one of A and B is methyl and the other is hydrogen, the wavy line represents R or S stereochemistry, n is 2 to 5, and R is hydrogen or lower alkyl having 1-7 carbon atoms.

2. A compound according to claim 1 of the formula

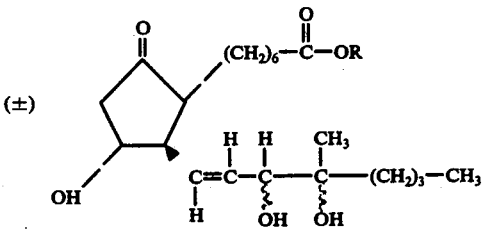

wherein R represents hydrogen or lower alkyl having 1-7 carbon atoms and the wavy line represents R or S stereochemistry.

3. A compound according to claim 1 which is racemic methyl 7-[(3α-hydroxy-2β-(4(RS)-hydroxy-4-methyl-3(S)-hydroxytrans-1octen-1-yl)-5-oxocyclopent-1α-yl]heptanoate.

4. A compound according to claim 1 which is racemic methyl 7-[(3α-hydroxy-2β-(4(RS)-hydroxy-4-methyl-3(R)-hydroxytrans-1-octen-1-yl)-5-oxocyclopent-1α-yl]heptanoate.

* * * * *